United States Patent [19]

Ranadive et al.

[11] Patent Number: 5,208,008

[45] Date of Patent: May 4, 1993

[54] REGIOSELECTIVE CHEMICAL MODIFICATION OF MONOCLONAL ANTIBODIES

[75] Inventors: Girish Ranadive; Howard S. Rosenzweig; Michael Epperly; William Bloomer, all of Pittsburgh, Pa.

[73] Assignee: University of Pittsburgh, Pittsburgh, Pa.

[21] Appl. No.: 613,127

[22] Filed: Nov. 14, 1990

[51] Int. Cl.$^5$ .................. A61K 49/02; C07K 15/28; C07K 15/02

[52] U.S. Cl. ................... 424/1.1; 530/388.1; 530/391.1; 530/391.3; 530/391.5; 530/391.7; 530/391.9; 424/9; 424/85.91; 435/7.1; 436/512

[58] Field of Search ............ 530/388, 389, 390, 391, 530/387, 388.1, 391.5, 391.9, 391.1, 391.3, 391.7; 424/1.1, 85.91; 435/7.1; 436/512

[56] References Cited

U.S. PATENT DOCUMENTS 4,671,958 6/1987 Rodwell et al. ............... 424/85.91

FOREIGN PATENT DOCUMENTS 0294294 12/1988 European Pat. Off. .
8706837 11/1987 World Int. Prop. O. .

OTHER PUBLICATIONS

Nanda et al. (1989) J. Neurosurg. 71:892–897.
Ahmad et al. (1988) Trends in Biotech. 6:246–251.
Blair et al. (1983) J. Immunol. Methods 59:129–143.
*Dictionary of Immunology*, W. Herbert et al., eds., Blackwell Scientific Publications 1985, Oxford, pp. 80–81.
Ghose et al. (1983) Methods Enzymol. 93:280–333.
Simonson et al. (1988) Clin. Chem. 34/9:1713–1716.

*Primary Examiner*—Christine M. Nucker
*Assistant Examiner*—Kay K. Kim
*Attorney, Agent, or Firm*—Reed Smith Shaw & McClay

[57] ABSTRACT

A method of selectively modifying an immunoglobulin having at least one Fab region and at least one Fc region, each region having an isoelectric point wherein said isoelectric point of the Fab fragment of said immunoglobulin is different than the isoelectric point of the Fc fragment of the immunoglobulin, said method comprising modification of the immunoglobulin at a pH between the respective isoelectric points of the Fab and Fc fragments of the immunoglobulin.

39 Claims, 4 Drawing Sheets

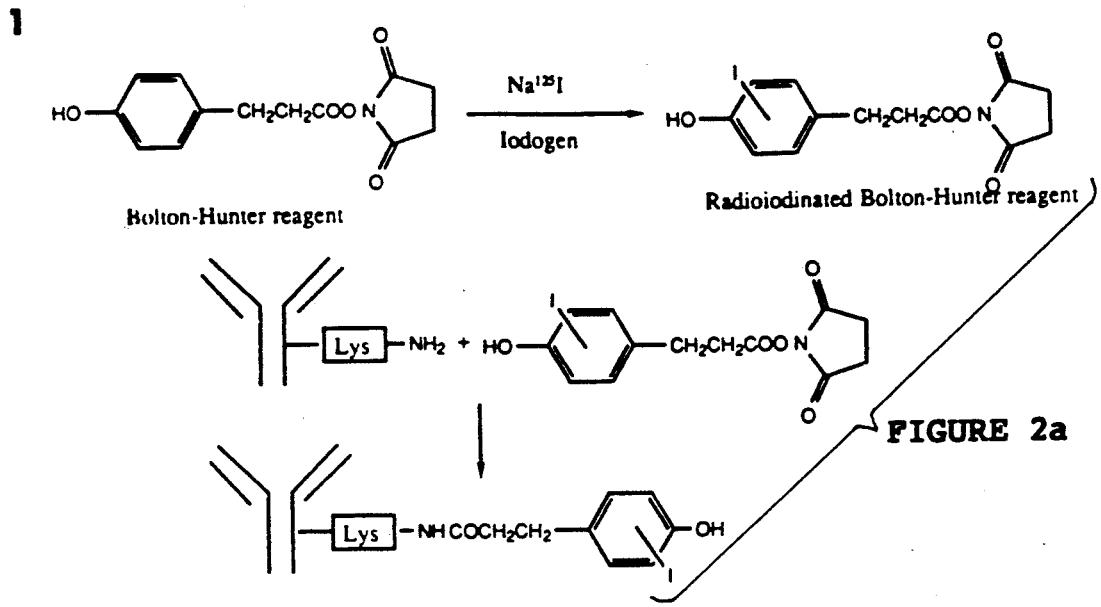
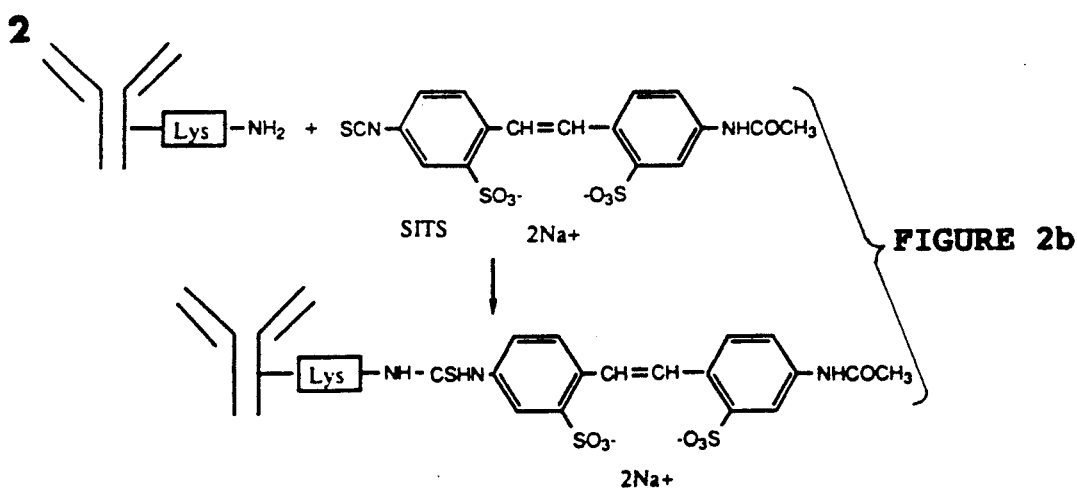
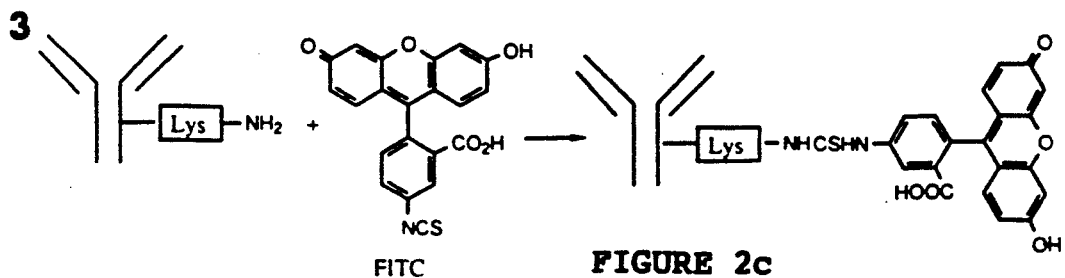

FIGURE 5a  FIGURE 5b  FIGURE 5c
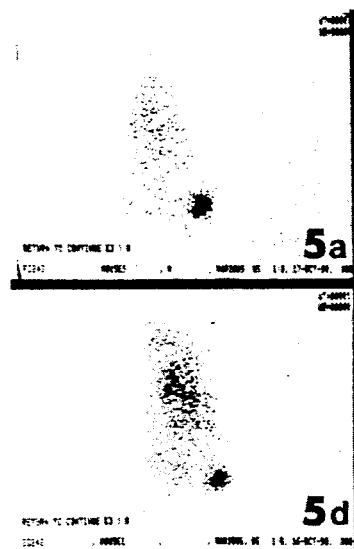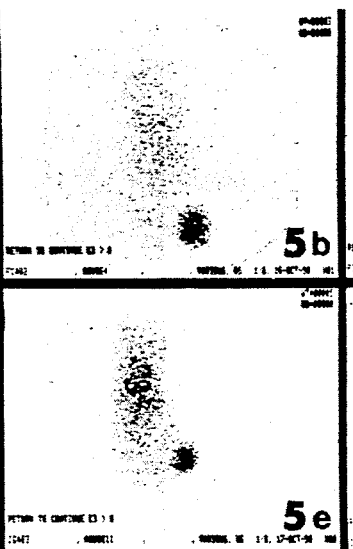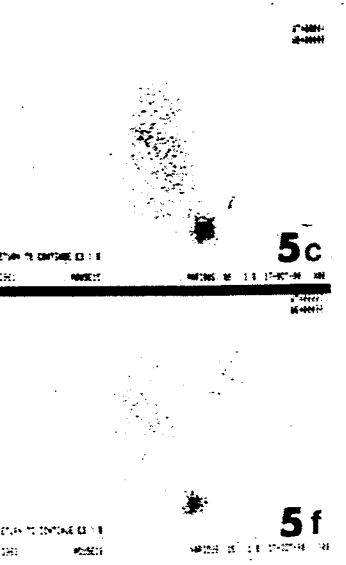
FIGURE 5d  FIGURE 5e  FIGURE 5f
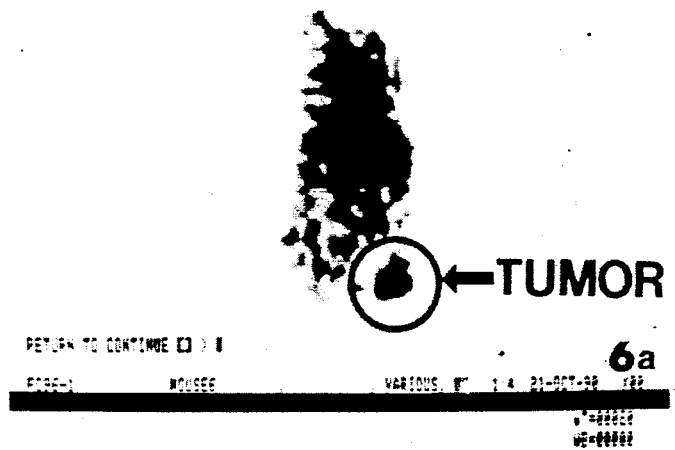
FIGURE 6a
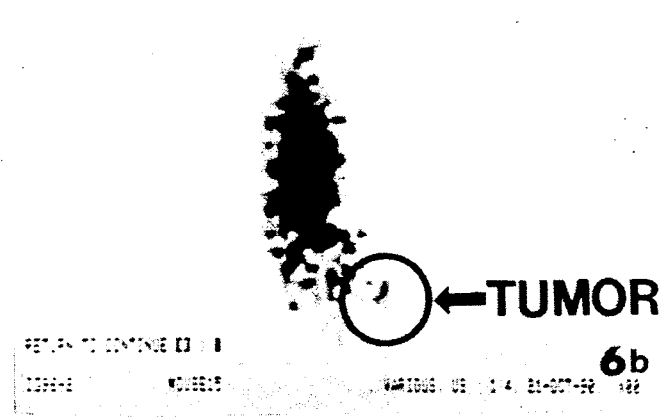
FIGURE 6b

REGIOSELECTIVE CHEMICAL MODIFICATION OF MONOCLONAL ANTIBODIES

ACKNOWLEDGMENT

The present invention was developed in part under Grant No. DE-FG02-89ER60869 of the United States Department of Energy. The Government has certain rights to this invention.

FIELD OF THE INVENTION

The present invention relates generally to chemical modification of immunoglobulins, and more particularly is directed to chemical modification of the Fc region of monoclonal antibodies.

BACKGROUND OF THE INVENTION

Chemical modifications of protein molecules usually involve reactions with specific amino acids such as lysine or tyrosine. However, such modifications are likely to damage the biological function, activity or specificity of the protein if the modifications occur at biologically active sites. Alteration of a protein's biological function(s) which results from chemical modification of the protein depends on the number and location of modified amino acids within its allosteric and/or active sites.

The development of monoclonal antibodies through hybridoma technology has made possible the production and isolation of large quantities of homogeneous antibody to defined antigenic determinants such as, for example, membrane surface features unique to tumor tissue. Thus, linking of radionuclides, toxins, chemotherapeutic agents, or fluorescent agents or compounds to monoclonal antibodies against antigenic determinants associated with a particular tumor is desirable for tumor imaging or therapy.

Antibodies in general, and monoclonal antibodies (MAb) in particular, are members of the class of complex proteins known as immunoglobulins and have a basic structure of two identical light and two identical heavy polypeptide chains joined together by interchain disulphide bonds in the form of a Y-shape as seen in FIG. 1. Treatment of an antibody with papain cleaves the molecule into three fragments or regions, two of which fragments bind to antigens (Fab) and one fragment which is readily crystallizable (Fc). The amino acid sequence of the N-terminal end of each of the chains varies greatly between molecules and is thus known as the variable region. The Variable regions of the two heavy and light chains are denoted $V_H$ and $V_L$ respectively. Each variable region of each chain also contains three hypervariable regions which are more variable than other regions in terms of amino acid substitutions, deletions, and insertions. The $V_H$ and $V_L$ domains are folded in such a way that the hypervariable regions are brought together to form an antigen binding site. The specificity of the antigen binding site is determined by the amino acid sequence of both the heavy and light chains. All antibody molecules, except for those of the IgM class, have two identical antigen binding sites.

As is well known in the art, one of the more preferred ways to attach a drug, toxin or radiolabeled compound to an immunoglobulin, such as a monoclonal antibody, is via a covalent linkage to the lysine residues of the immunoglobulin. See. Koppel, G. A., *Bioconjugate Chem.* 1:13-23 (1990), the disclosure of which is incorporated herein by reference. A major drawback to this method of protein modification is that the epsilon-amino group of lysines in the Fab portion will be altered, and if one of such group is essential for the binding to a particular antigen, the immunoreactivity of the monoclonal antibody will be degraded, if not completely lost. In such an instance the resulting drug, toxin, or radiolabeled monoclonal antibody conjugate is rendered highly ineffective, if not useless.

Previous methods of selective modification of immunoglobulins have been limited because they have been directed to modification of those immunoglobulins with sugar residues attached to the Fc region.

It is therefore desirable to modify intact monoclonal antibodies at specific sites to allow for the coupling of diagnostic or therapeutic agents without significantly diminishing immunoreactivity.

It is also desirable to modify monoclonal antibodies at specific sites regardless of whether the antibody has sugar residues.

In the following description of the present invention, the term "biodistribution" refers to the distribution of antibody in a subject to which antibody has been administered. By contrast, "uptake" refers to the quantity of antibody in a given tissue.

SUMMARY OF THE INVENTION

Accordingly, it is a primary object of the present invention to selectively modify immunoglobulins without significantly reducing immunoreactivity.

Another object of the present invention is to selectively couple radiolabels, drugs, toxins, or fluorescent agents to monoclonal antibodies while retaining the immunoreactivity of the monoclonal antibody.

Another aspect of the invention is to be able to modify antibodies at specific sites regardless of whether the antibody has sugar residues.

These and other objects of the present invention are achieved by one or more of the following embodiments.

In one aspect, the invention features a method of selectively modifying an immunoglobulin having at least one Fab region and at least one Fc region, each region having an isoelectric point wherein the isoelectric point of the Fab fragment of said immunoglobulin is different than the isoelectric point of the Fc fragment of the immunoglobulin, said method comprising modification of the immunoglobulin at a pH between the respective isoelectric points of the Fab and Fc fragments of the immunoglobulin.

In another aspect, the invention features a method of enhancing the biodistribution of immunoglobulin having a Fab region and a Fc region for localization in a target, comprising exposing a mammalian subject to immunoglobulin that has been chemically modified at only its Fc region.

In a third aspect, the invention features a method of producing chemically modified immunoglobulin having a Fab and a Fc region with improved immunoreactivity comprising the steps of determining the individual isoelectric of the Fc and Fab fragments of the immunoglobulin; and performing a chemical modification of said immunoglobulin at a pH within the range of the two isoelectric points.

In preferred embodiments of the method, the immunoglobulin is an antibody, and is more preferably a monoclonal antibody.

Other features and advantages of the invention will be apparent from the following description of the preferred embodiment, and from the claims.

DESCRIPTION OF THE DRAWINGS

FIGS. 2a-2c show schematic reaction pathways for modifying antibody molecules with radioiodinated Bolton-Hunter reagent, SITS, and FITC respectively.

FIGS. 5a-5f are a set of photographs of gamma camera images of mice bearing subcutaneous LS 174T xenografts treated with B72.3 MAb labeled with $^{125}$I either indiscriminately (5d, 5e, 5f) or on the Fc fragment (5a, 5b, 5c) of the MAb, and imaged at 24, 48, and 96 hours post-injection, respectively.

FIGS. 6a and 6b are a set of photographs of gamma camera images of mice bearing subcutaneous U-87 MG xenografts treated with AY-1 MAb labeled either indiscriminately (6b) or on the Fc fragment (6a) of the MAb with $125_I$ and imaged 96 hours post-injection.

DETAILED DESCRIPTION OF THE INVENTION

Figure 1:
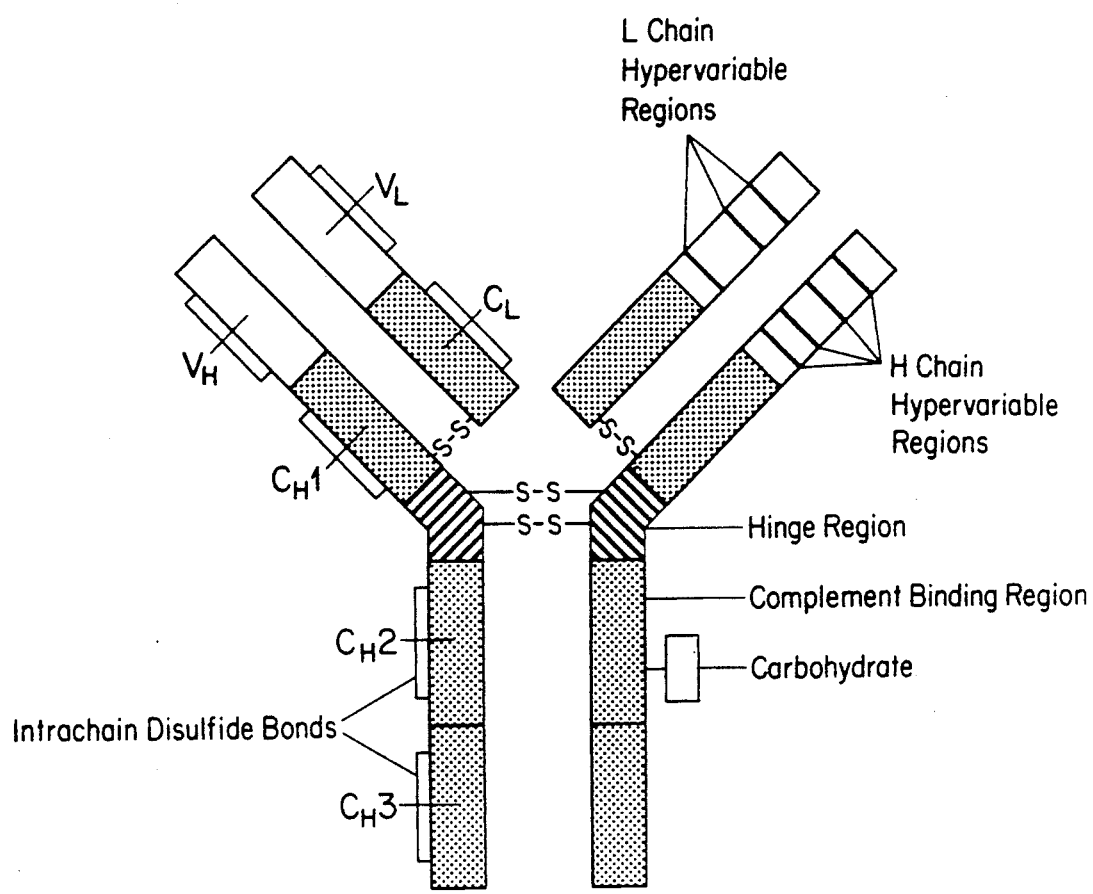
FIG. 1 shows the basic structure of monoclonal antibodies and other immunoglobulins.

The presently claimed invention provides a method for selectively modifying the non-immunoreactive Fc region amino acid residues of an intact immunoglobulin, preferably a monoclonal antibody. The present method is based on the properties of antibodies and monoclonal antibodies, namely, that the N-terminal Fab regions of antibodies are often more basic than the C-terminal Fc regions of antibodies. See, Gooling, J. W., *Monoclonal Antibodies: Principles & Practice* Academic Press, N. Y., 99-133 (1983), the disclosure of which is incorporated herein by reference. The foregoing general property of antibodies means that the isoelectric point (pI), the pH at which the mean charge of a protein is zero, of the Fab fragments of a particular antibody is different from the pI of the Fc fragment. In particular, the pI of the Fab regions is generally higher than the pI of the Fc region or fragment of the same antibody.

According to the method of the present invention, immunoglobulins are chemically modified at a pH between the respective pI values for the Fab and Fc fragments, and preferably at about the midpoint of the pI values of the Fc and Fab fragments. The preferred difference in the pI values of the Fab fragment and the Fc fragment is greater than or equal to about 1 and is typically between about 1 and 2.5. Under such conditions, amino acid residues in the Fc region such as lysine can be selectively subjected to chemical modification because the same amino acid residues in the Fab regions are at a pH below their pI, the result of which is that the lysine residues are protonated and unreactive.

Comparison testing of monoclonal antibodies radiolabeled or labeled with fluorescent compounds according to the methods of the present invention, and by conventional method as shown in the following examples, demonstrates that immunoreactivity is retained to a much higher level when the antibodies are labeled according to the present methods. Thus the present method of regioselectively modifying immunoglobulins can be advantageously used to increase the specificity of antibodies used both in diagnostic testing, in vivo or in vitro and in therapy.

In general, the method of the present invention is useful for site specific modification of the IgG class and other classes of immunoglobulins. In particular sugar residues are not required to be present on the antibody. The method of the present invention can be used to modify immunoglobulins with a variety of substances that include radionuclides such as halogens and astatine, toxins such as ricin and diphtheria toxin, drugs such as chemotherapeutic agents including methotrexate and vinblastine and fluorescent agents or tags such as SITS and FITC. Such substances may, depending on structure, be directly covalently linked to lysine residues or they may be attached to the antibodies via chelating agents that can be covalently bonded through lysine.

While the method of the present invention most readily lends itself to the selective modification of immunoglobulins for use in tumor imaging and tumor therapy, other types of targets, in addition to tumors, for which the modified immunoglobulins of the present method may be used include bacteria, viruses, hematapoietic cells such as lymphocytes or selected classes thereof, and blood clots and injured or damaged tissues such as myocardoium.

EXAMPLES

EXAMPLE 1

B72.3 antibody (ATCC cat. no. HB8108) shows a high degree of specificity for mammary and colon carcinomas. See. Colcher, D. et al, *Cancer Research* 44: 5744-5751 (1984), the disclosure of which is incorporated herein by reference. B72.3 monoclonal antibody, a gift from Dr. Jeffrey Schlom of the National Cancer Institute (Bethesda, MD), was isolated from ascites fluid. The antibody was partially purified according to the method of Colcher, D., et al, *Cancer Research* 44: 5744-5751 1984) via ammonium sulfate precipitation followed by DEAE-52 anion exchange chromotography. The antibody was further purified by fast protein liquid chromotography (FPLC) using a MONO Q HR 5/5 column (Pharmacia) with a 0 to 0.5M NaCl linear gradient in 20 mM TRIS chloride at pH 7.7 as described by Taska, K., et al, *Acta Histochem* 17: 283-286 (1984), the disclosure of which is incorporated herein by reference.

After the B72.3 antibody was digested with papain, the Fab and Fc fragments were isolated using a protein A-sepharose column according to the methods of Davies, M.E., et al, *J. Immunol Methods* 21: 305-315 (1978), the disclosure of which is incorporated herein by reference.

Human antiglioblastoma monoclonal antibody AY-1 as described by Nanda, A., et al, *J. Neurosuro* 71: 892-897 (1989), the disclosure of which is incorporated herein by reference, was a gift from Dr. Anil Nanda, Department of Surgery, Louisiana State University Medical Center (Shreveport, La.).

Na$^{125}$I (14 mCi/mg) was obtained from Amersham Corporation (Arlington, Ill.). Iodogen and 1-ethyl-3-(3-dimethylaminopropyl) carbodiimide hydrochloride (EDC) were obtained from Pierce (Rockford, Ill.) and fluorescent imaging compounds SITS and FITC were obtained from Molecular Probes (Eugene, OR). All reagents and buffers were of analytical grade.

The pI of Fab and Fc fragments were determined by electrophoresis using an isoelectric focusing phastgel system, gels, calibration kit and markers from Pharmacia LKB (Piscataway, N.J.).

B72.3 monoclonal antibody was radioiodonated using the Bolton-Hunter reagent as reported by Bolton, A. E., et al, *Biochem, J.* 33: 529-539 (1973), the disclosure of which is incorporated herein by reference, and modified as described herein. The reaction pathway is.. schematically shown in section 1 of FIG. 2a. Bolton-Hunter reagent (0.4 mg) was iodinated using 1.5 mCi Na$^{125}$I and Iodogen as described in Colcher, D., et al., *Cancer Research* 44: 5744-5751 (1984). The reaction product was extracted twice with benzene. The benzene extraction layer was evaporated to dryness. The resulting succinimidyl activated ester of the Bolton-Hunter reagent is hydrolyzed during the reaction thereby lowering the iodine incorporation into antibody. The yield of iodinated antibody was improved, however, by adding one mole equivalent of EDC and N-hydroxysulfosuccinimide to the reaction mixture to regenerate in situ the activated ester. It was then reacted with B72.3 MAb (200 ug) in 0.5 mM sodium acetate (50 mM) containing 50 mM NaCl at pH 6.2.

Radioiodination of AY-1 monoclonal antibody using Na$^{125}$I was accomplished analogously to the method described for B72.3 Mab except that the reaction was carried out in 0.1 M borate buffer at pH 7.6.

Labelling of the B72.3 MAb with the SITS (p-acetamido-4'-isothiocyanatostilbene-2,2'-disulfonic acid, disodium salt) fluorescent label or tag was carried out as follows. B72.3 MAb (1 mg) was modified with a 10-fold molar excess of SITS in 0.5 ml of 50 mM acetate buffer containing 50 mM sodium chloride at pH 6.2. The reaction mixture was stirred at 4° C. for 4 hours and passed through a Sephadex G-25 column. The labeled antibody was eluted with the void volume and was concentrated by ultrafiltration with Centricon-10 (MWCO 10,000, Amicon Corp, Danvers, Mass.). The reaction pathway is shown in part 2 of FIG. 2b.

AY-1 antibody was similarly labeled with the FITC (fluorescein 5-isothiocyanate) fluorescent label in borate buffer (0.1 M) at pH 7.4 and at pH 9.3. The reaction pathway is shown in part 3 in FIG. 2c. Fab and Fc fragments of the fluorescent and radiolabeled monoclonal antibodies were obtained by first digesting the antibodies with papain and then by purifying the resulting fragments over a protein A-sepharose column. FPLC was then performed on a MONO Q HR 5/5 column according to the method of Taska, K., et al, *Acta Histochem. Cytochem.* 17: 283-286 (1984).

Fluorescence measurements were carried out on a Perkin-Elmer MPF 66 Spectrofluorimeter programmed with IDRIS computer software (Perkin Elmer, Norwalk, Conn.) for data acquisition and manipulation. The excitation and emission slit width were 5 nm each for these measurements. SITS-modified protein was excited at 336 nm and the emission spectrum scanned between 400 and 450 nm. FITC modified protein was excited at 494 nm and the emission spectrum scanned between 500 to 550 nm. Radioactive counting for $^{125}$I labeled samples were carried out on a Packard Auto-gamma 5650 gamma counter (Packard, Downers Grove, Ill.).

The pI values of Fc and Fab fragments of B72.3 and AY-1 monoclonal antibodies were measured and are shown in Table 1 below. As can be seen, the pI values of the Fab fragments of the B72.3 and AY-1 monoclonal antibodies are greater than the pI values of the Fc fragments of the respective monoclonal antibodies.

TABLE 1

| pI | B72.3 | AY-1 |
|---|---|---|
| Fab | 6.78 | 8.45 |
| Fc | 5.73 | 6.35 |

EXAMPLE 2

The modification described in Example 1 for the Bolton-Hunter (B-H) reagent was also carried out with the B72.3 monoclonal antibody and SITS in place of the B-H reagent at pH 6.2. The reaction pathway is shown in section 2 of FIG. 2b. Under these reaction conditions, the epsilon-amino side chain residues of lysines in Fab region were protonated.

Figure 3:
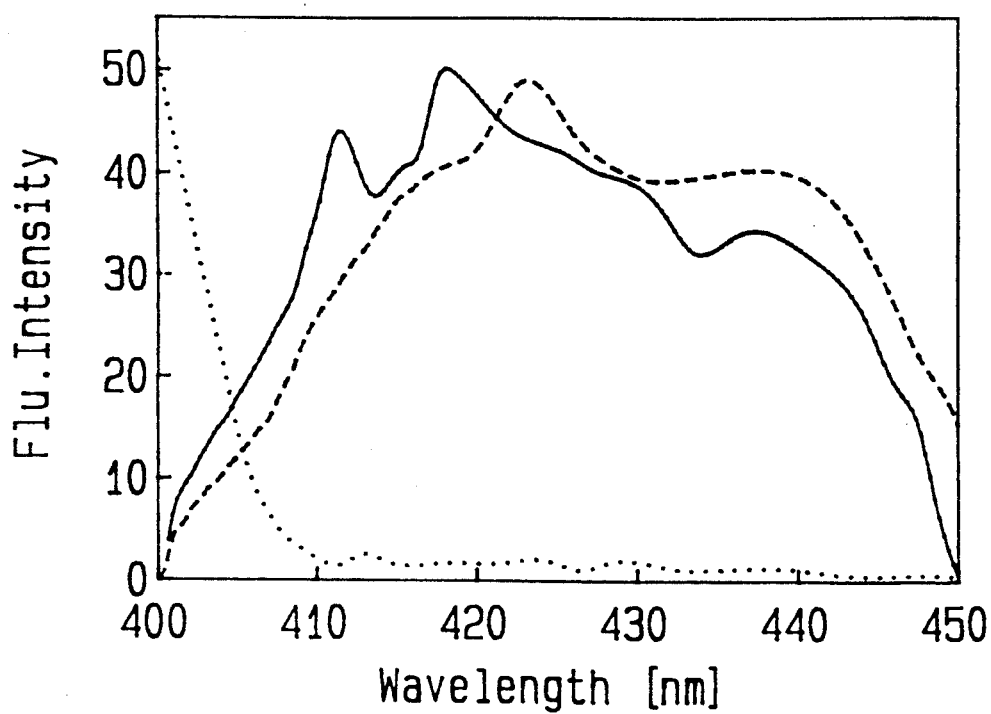
FIG. 3 is a graph showing the emission spectra of Fc and Fab fragments of SITS modified B72.3 MAb.

FIG. 3 shows the fluorescence emission spectrum at 336 nm excitation of SITS in water (solid line) as well as the emission spectra of Fc (dashed line) and Fab (dotted line) fragments of SITS modified B72.3 monoclonal antibody. The Fab fragments of SITS-modified B72.3 showed almost no fluorescence as compared to the incorporation of SITS into the Fc region of the antibody.

Similarly, when the B72.3 antibody was radiolabeled with 125I as described in Example 1, 88% of counts (29,871) were found in the Fc fragment of B72.3, compared to 12% in the Fab fragment (3715 counts).

EXAMPLE 3

Figure 4:
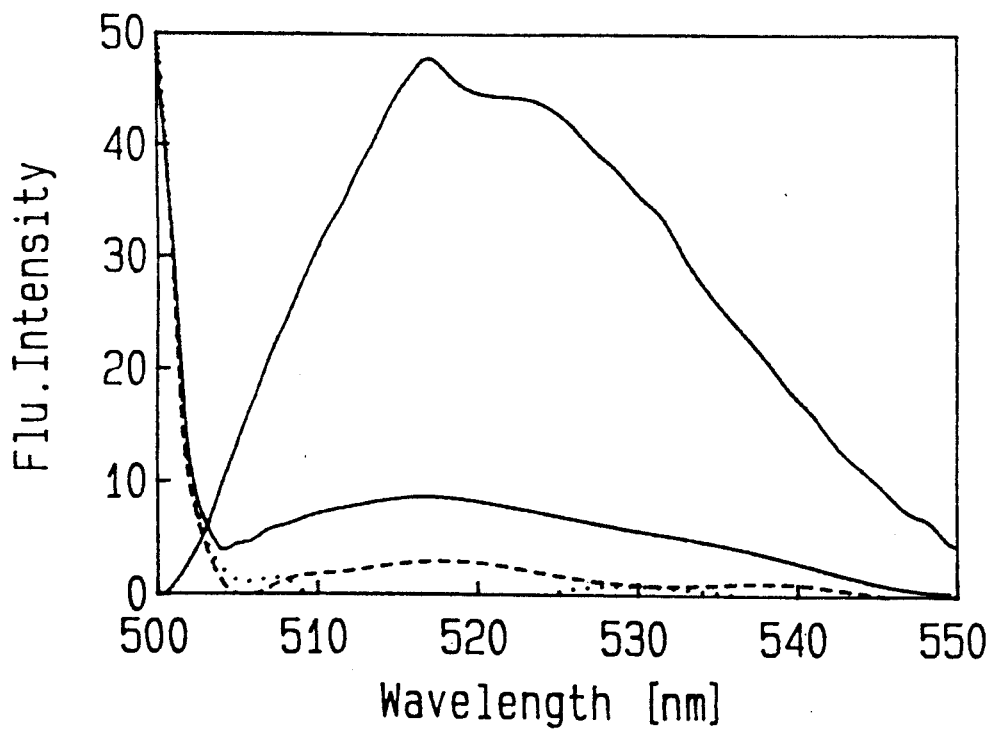
FIG. 4 is a graph showing the emission spectra of FITC modified whole AY-1 MAb and Fab fragments of FITC modified AY-1 MAb.

Negative control experiments were performed with the AY-1 antibody. As shown in FIG. 4, fluorescence emission spectra were measured for FITC alone (2 uM, pH 8.0) (solid line with intense fluorescence), and AY-1 monoclonal antibody modified with FITC at pH 9.3 before digestion with papain (solid line with weak fluorescence). Fluorescence emission spectra at 494 nm excitation are shown for the Fab fragment of FITC tagged AY-1 monoclonal antibody carried out at pH 9.3 (dashed line) and the Fab fragment of the AY-1 monoclonal antibody modified at pH 7.3 (dotted line barely visible along the abscissa). The spectra show that all the lysine residues of the Fab region were protected from chemical attack when the modification was performed at pH 7.3, because the Fab fragments did not fluoresce. On the other hand, when the FITC modification was carried out at pH 9.3, FITC was more readily incorporated in the Fab region of antibody (dashed line).

Radiolabeling experiments analogous to those performed with B72.3 were performed. AY-1 monoclonal antibody was radioiodinated at a pH between the pI values of Fab and Fc fragments, pH 7.6, and the antibody was then digested with papain. 90% of radioactivity (16,900 counts) was found in the Fc fragment compared to 10% in the Fab fragment (1690 counts).

In the following example, biodistribution of B72.3 and AY-1 MAbs were determined.

EXAMPLE 4

Athymic nude mice (Harlan Sprague Dawley, Indianapolis, Ind.) were injected subcutaneously in the right rear leg with $1 \times 10^7$ cells of either the LS 174T human adenocarcinoma of the colon cell line (ATCC CL 188) or the U-87 MG human glioma cell line (ATCC HTB 14). When the tumor xenografts had reached a size of about 1 cm by 1 cm (in about one week), the mice bearing the LS 174T tumor were injected intravenously via the tail vein with $^{125}$I-B72.3 monoclonal antibody labeled discriminately on the Fc region or indiscriminately on the whole antibody. Similarly, the mice bearing the U-87 MG xenografts were injected intravenously with the $^{125}$I-AY-1 labeled discriminately on the Fc portion or indiscriminately after about three weeks when the tumor xenografts had reached a size of about 1 cm by 1 cm. At 24, 48 and 96 hours after injection, three mice were sacrificed at each time point and scanned under a gamma camera. To prevent uptake of free $^{125}$I by the thyroid, the mice had potassium iodide added to their drinking water to block uptake by the thyroid. Various organs were removed, weighed and counted in a Packard gamma counter. The counts were converted into disintegrations per minute (DPM) and data recorded as DPM/gram of tissue, percent of the injected dose per gram of tissue, and the ratio of percent injected dose per gram of tumor to the percent injected dose per gram of normal tissue (tumor/tissue ratios). The results are shown in Table 2.

TABLE 2

| | Iodination Of B72.3: | | | |
|---|---|---|---|---|
| | In Fc Fragment | | In Indiscriminate | |
| Tissue | Tumor/Tissue Ratio | % Injected Dose | Tumor/Tissue Ratio | % Injected Dose |
| | 24 Hours Post Injection: | | | |
| Brain | 32.5 ± 10.6 | 0.2 ± 0.1 | 24.1 ± 0.7 | 0.6 ± 0.1 |
| Blood | 2.3 ± 0.2 | 3.4 ± 1.7 | 2.3 ± 0.5 | 6.0 ± 0.3 |
| Liver | 4.8 ± 0.7 | 1.6 ± 0.7 | 5.9 ± 0.1 | 2.4 ± 0.4 |
| Stomach | 33.5 ± 9.3 | 0.2 ± 0.1 | 36.3 ± 6.9 | 0.4 ± 0 |
| Gut | 25.9 ± 2.1 | 0.3 ± 0.2 | 18.5 ± 4.0 | 0.8 ± 0.02 |
| Kidney | 5.1 ± 1.0 | 1.5 ± 0.6 | 6.4 ± 1.2 | 2.2 ± 0 |
| Bone | 16.8 ± 3.8 | 0.4 ± 0.2 | 18.6 ± 3.3 | 0.76 ± 0.01 |
| Tumor | — | 8.02 ± 4.1 | — | 14.17 ± 2.7 |
| | 48 Hours Post Injection: | | | |
| Brain | 48.1 ± 11.8 | 0.1 ± 0.01 | 45.9 ± 10.0 | 0.3 ± 0.1 |
| Blood | 2.6 ± 0.2 | 2.7 ± 0.6 | 2.9 ± 0.4 | 3.8 ± 0.8 |
| Liver | 7.1 ± 0.5 | 1.0 ± 0.1 | 5.9 ± 0.5 | 1.9 ± 0.5 |
| Stomach | 41.5 ± 6.1 | 0.2 ± 0.01 | 46.9 ± 10.5 | 0.3 ± 0.2 |
| Gut | 19.6 ± 1.7 | 0.4 ± 0.04 | 26.9 ± 3.4 | 0.4 ± 0.1 |
| Kidney | 7.5 ± 0.3 | 0.9 ± 0.2 | 6.7 ± 0.6 | 1.7 ± 0.4 |
| Bone | 22.4 ± 2.4 | 0.3 ± 0.1 | 22.4 ± 0.4 | 0.5 ± 0.2 |
| Tumor | — | 7.11 ± 1.4 | — | 11.3 ± 3.7 |
| | 96 Hours Post Injection: | | | |
| Brain | 82.2 ± 13.3 | 0.2 ± 0.1 | 77.8 ± 15.1 | 0.1 ± 0.05 |
| Blood | 4.0 ± 0.9 | 3.4 ± 2.0 | 4.6 ± 0.2 | 1.5 ± 0.9 |
| Liver | 9.4 ± 1.6 | 1.4 ± 0.7 | 9.2 ± 0.6 | 0.8 ± 0.4 |
| Stomach | 61.3 ± 9.3 | 0.2 ± 0.1 | 69.1 ± 21.1 | 0.1 ± 0.01 |
| Gut | 42.1 ± 1.9 | 0.3 ± 0.1 | 32.3 ± 3.5 | 0.2 ± 0.1 |

TABLE 2-continued

| | Iodination Of B72.3: | | | |
|---|---|---|---|---|
| | In Fc Fragment | | In Indiscriminate | |
| Tissue | Tumor/Tissue Ratio | % Injected Dose | Tumor/Tissue Ratio | % Injected Dose |
| Kidney | 11.0 ± 2.1 | 1.2 ± 0.7 | 11.1 ± 0.5 | 0.6 ± 0.3 |
| Bone | 30.9 ± 5.8 | 0.4 ± 0.2 | 34.3 ± 2.7 | 0.2 ± 0.1 |
| Tumor | — | 12.08 ± 4.2 | — | 6.88 ± 3.7 |

Note: Results were obtained from N = three mice per time point.

Table 2 shows that the discriminate labeling of the B72.3 antibody has no serious negative effects on the binding of the B72.3 in vivo. The B72.3 label on the Fc portion yielded the same tumor/tissue ratios as the indiscriminately labeled B72.3 antibody. The high tumor/tissue ratios shown in the first and third columns of Table 2 indicate the specificity of the antibody since antibodies with little specificity for the tumor cells will bind nonspecifically to normal cells at the same rate as to tumor cells and thus yield low tumor/tissue ratios. High values for the percent injected dose do not necessarily indicate the specificity or the ability of the antibody to bind to tumor cells since high percent injected doses in all tissues will yield low tumor/tissue ratios. Ideally, what is desired is low percent injected doses in all tissues except the tumor where a high percent injected dose is desired. This will result in high tumor/tissue ratios. Only in the cases of the liver at 24 and 48 hours after injection and in the gut at all three time points is there a significant difference in the tumor/tissue ratio. Also, as seen in FIGS. 5a-5f, gamma camera scans of the mice indicate no apparent gross differences in the uptake of the two labeled antibodies by the tumor xenograft or the normal organs of the mouse.

Table 3 shows the results of the biodistribution studies using $^{125}$I-AY-1 MAb. As can be readily seen, the biodistribution is enhanced since the discriminately labeled antibody is taken up by the tumor to a greater degree than the indiscriminately labeled antibody. FIG. 6 shows gamma camera scans of two mice with approximately the same size tumor. The tumor in the mouse injected with the discriminately labeled AY-1 is easily recognized while the tumor in the mouse injected with the indiscriminately labeled AY-1 is barely detectable.

TABLE 3

| | Iodination Of AY-1 In: | | | | |
|---|---|---|---|---|---|
| | Fc Fragment | | Indiscriminate | | |
| Tissue | Tumor/Tissue Ratio (TTFc) | % Injected Dose | Tumor/Tissue Ratio (TTI) | % Injected Dose | TTFc/TTI |
| | 24 Hours Post Injection: | | | | |
| Brain | 66.5 ± 43.0 | 0.2 ± 0.05 | 10.6 ± 2.1 | 0.3 ± 0.1 | 5.3 |
| Blood | 6.6 ± 4.7 | 2.1 ± 0.8 | 0.8 ± 0.3 | 4.0 ± 1.4 | 7.0 |
| Liver | 7.5 ± 4.1 | 1.5 ± 0.2 | 1.1 ± 0.2 | 2.8 ± 0.2 | 6.4 |
| Stomach | 20.3 ± 15.3 | 0.8 ± 0.3 | 2.3 ± 0.4 | 1.3 ± 0.1 | 10.4 |
| Gut | 26.7 ± 18.4 | 0.5 ± 0.2 | 2.5 ± 0.6 | 1.2 ± 0.2 | 8.2 |
| Kidney | 9.0 ± 5.4 | 1.3 ± 0.2 | 1.2 ± 0.2 | 2.5 ± 0.1 | 6.7 |
| Bone | 28.5 ± 15.3 | 0.4 ± 0.04 | 3.1 ± 0.7 | 1.0 ± 0.2 | 9.0 |
| Tumor | — | 10.5 ± 4.8 | — | 3.0 ± 0.5 | — |
| | 48 Hours Post Injection: | | | | |
| Brain | 13.8 ± 3.1 | 0.2 ± 0.02 | 10.3 ± 3.8 | 0.3 ± 0.1 | 2.9 |
| Blood | 0.7 ± 0.1 | 3.6 ± 0.4 | 0.6 ± 0.1 | 3.8 ± 0.3 | 1.2 |
| Liver | 0.9 ± 0.1 | 2.5 ± 0.1 | 1.0 ± 0.2 | 2.4 ± 0.4 | 1.0 |
| Stomach | 4.9 ± 0.8 | 0.5 ± 0.1 | 3.6 ± 1.3 | 0.7 ± 0.2 | 0.7 |
| Gut | 4.4 ± 0.4 | 0.6 ± 0.1 | 3.8 ± 0.4 | 0.6 ± 0.01 | 1.2 |
| Kidney | 1.6 ± 0.2 | 1.6 ± 0.2 | 1.4 ± 0.2 | 1.7 ± 0.1 | 0.9 |
| Bone | 4.3 ± 0.2 | 0.6 ± 0.1 | 3.3 ± 0.4 | 0.7 ± 0.1 | 1.3 |
| Tumor | — | 2.45 ± 0.18 | — | 2.3 ± 0.2 | — |
| | 96 Hours Post Injection: | | | | |

TABLE 3-continued

| | Iodination Of AY-1 In: | | | | |
| | Fc Fragment | | Indiscriminate | | |
| Tissue | Tumor/Tissue Ratio (TTFc) | % Injected Dose | Tumor/Tissue Ratio (TTI) | % Injected Dose | TTFc/TTI |
| --- | --- | --- | --- | --- | --- |
| Brain | 19.7 ± 5.8 | 0.2 ± 0.01 | 10.4 ± 07.6 | 0.4 ± 0.3 | 4.1 |
| Blood | 2.0 ± 0.4 | 1.5 ± 0.1 | 0.6 ± 0.1 | 2.9 ± 0.1 | 3.5 |
| Liver | 2.4 ± 0.3 | 1.2 ± 0.2 | 1.5 ± 0.3 | 1.2 ± 0.2 | 1.6 |
| Stomach | 10.1 ± 1.5 | 0.3 ± 0.03 | 3.8 ± 0.8 | 0.5 ± 0.1 | 2.8 |
| Gut | 10.1 ± 1.9 | 0.3 ± 0.03 | 5.1 ± 1.2 | 0.4 ± 0.1 | 2.1 |
| Kidney | 3.1 ± 0.4 | 0.9 ± 0.1 | 1.5 ± 0.1 | 1.2 ± 0.1 | 1.1 |
| Bone | 10.7 ± 2.1 | 0.3 ± 0.02 | 4.6 ± 0.5 | 0.4 ± 0.01 | 2.3 |
| Tumor | — | 3.03 ± 0.8 | — | 1.7 ± 0.2 | — |

Note: Results were obtained from N = three mice per time point.

Biodistribution studies shown in Table 3 also demonstrate a greater uptake in the tumor in mice injected with the discriminately labeled antibody. Significant differences in tumor/tissue ratios are seen for all organs at 24 hours after injection and all organs except the brain at 96 hours after injection with the ratios for the discriminately labeled antibody being higher than those for the indiscriminately labeled monoclonal antibody. The percent injected dose for all organs for the most part show no substantial differences.

There is a major difference in the percent injected dose for the tumor at 24 and 96 hours with the discriminately labeled antibody showing a higher percentage injected dose. This indicates that the binding ability of the discriminately labeled antibody is greater than that of the indiscriminately labeled antibody. This is to be expected since labeling with the Fab region which may occur in the indiscriminately labeled antibody is likely to alter the immunoreactive sites of the Fab region resulting in the loss of binding ability of the antibody. Thus the immunoreactivity of the immunglobulin is improved relative to conventional methodology.

Although the invention has been described in detail for the purposes of illustration, it is to be understood that such detail is solely for that purpose and that variations can be made therein by those skilled in the art without departing from the spirit and scope of the invention except as it may be limited by the claims.

What is claimed is:

1. A method of selectively modifying an immunoglobulin having at least one Fab region and at least one Fc region, each region having an isoelectric point wherein said isoelectric point of the Fab fragment of said immunoglobulin is different than the isoelectric point of the Fc fragment of immunoglobulin, said method comprising modification of the Fc region amino groups of the immunoglobulin at a pH between the respective isoelectric point of the Fab and Fc fragments of the immunoglobulin.

2. The method of claim 1, wherein said immunoglobulin is an antibody.

3. The method of claim 2, wherein said immunoglobulin is a monoclonal antibody.

4. The method of claim 3, wherein said monoclonal antibody is B72.3.

5. The method of claim 3, wherein said monoclonal antibody is human antiglioblastoma monoclonal antibody.

6. The method of claim 1, wherein the difference of values of said isoelectric points of the Fab and Fc fragments of said immunoglobulin is in the range of about 1.0 to about 2.0.

7. The method of claim 1, wherein the difference of the values of said isoelectric points of the Fab and Fc fragments of said immunoglobulin is greater than or equal to about 1.0.

8. The method of claim 1, wherein said modification comprises attachment of a compound containing a radionuclide suitable for gamma imaging to said immunoglobulin.

9. The method of claim 8, wherein said radionuclide comprises the group consisting of the halogens and astatine.

10. The method of claim 9, wherein said radionuclide is iodine-125.

11. The method of claim 1, wherein said modification comprises attachment of a toxin to said immunoglobulin.

12. The method of claim 11, wherein said toxin is diphtheria toxin or ricin.

13. The method of claim 1, wherein said modification comprises attachment of a drug to said immunoglobulin.

14. The method of claim 13, wherein said drug is a chemotherapeutic agent selected from the group consisting of methoxrexate and vinblastine.

15. The method of claim 1, wherein said modification comprises attachment of a fluorescent agent to said immunoglobulin.

16. The method of claim 15, wherein said fluorescent agent is SITS.

17. The method of claim 15, wherein said fluorescent agent is FITC.

18. The method of claim 1 wherein said method comprises modification of basic amino groups of the immunogloublin at a pH between the respective isoelectric points of the Fab and Fc fragments of the immunoglobulin.

19. The method of claim 10 wherein said method comprises modification of lysine groups of the immunoglobulin at a pH between the respective isoelectric points of the Fab and Fc fragments of the immunoglobulin.

20. The method of enhancing the biodistribution of immunoglobulin having a Fab region and an Fc region for localization in a target, comprising exposing a mammalian subject to immunoglobulin that has been chemically modified at only the Fc region amino groups of the immunoglobulin at a pH between the isoelectric points of the Fab and Fc fragments of the immunoglobulin.

21. The method of claim 20, wherein the difference of the values of said isoelectric points of the Fab and Fc fragments of said immunoglobulin is in the range of about 1.0 to about 2.0.

22. The method of claim 20, wherein the difference of the values of said isoelectric points of the Fab and Fc fragments of said immunoglobulin is greater than or equal to about 1.0.

23. The method of claim 20, wherein said immunoglobulin is an antibody.

24. The method of claim 23, wherein said antibody is a monoclonal antibody.

25. The method of claim 20, wherein said chemical modification comprises attachment of a compound containing a radionuclide to said immunoglobulin.

26. The method of claim 25, wherein said compound contains iodine-125.

27. The method of claim 20, wherein said chemical modification comprises attachment of a toxin to said immunoglobulin.

28. The method of claim 20, wherein said chemical modification comprises attachment of a drug to said immunoglobulin.

29. The method of claim 28, wherein said modification is performed at a pH at about the midpoint of the pI values of the Fc and Fab fragments.

30. The method of claim 28, wherein said immunoglobulin is a monoclonal antibody.

31. The method of claim 20, wherein said chemical modification comprises attachment of a fluroescent agent to said immunoglobulin.

32. The method of claim 20 wherein said method comprises exposing a mammalian subject to immunoglobulin that has been chemically modified at only Fc basis amino groups of the immunoglobulin.

33. The method of claim 32 wherein said method comprises exposing a mammalian subject to immunoglobulin that has been chemically modified at only lysine groups of the immunoglobulin.

34. A method of producing chemically modified immunoglobulin having a Fab region and an Fc region with improved immunoreactivity comprising the steps of:

determining the individual isoelectric points of the Fc and Fab fragments of the immunoglobulin; and performing a chemical modification of Fc region amino groups of said immunoglobulin at a pH within the range of the two isoelectric points.

35. The method of claim 34 wherein said method comprises performing a chemical modification of Fc region basic amino groups of said immunoglobulin at a pH within the range of the two isoelectric points.

36. The method of claim 35 wherein said method comprises performing a chemical modification of Fc region lysine groups of the immunoglobulin at a pH within the range of the two isoelectric points.

37. A method of enhancing the sensitivity of an immunoglobulin having a Fab region and an Fc region for use in diagnostic testing using a target, said method comprising exposing the target to an immunoglobulin that has been chemically modified at only Fc region amino groups of the immunoglobulin at a pH between the isoelectric points of the Fab and Fc fragments of the immunoglobulin.

38. The method of claim 37 wherein said method comprises exposing the target to an immunoglobulin that has been chemically modified at Fc region basic amino groups of the immunoglobulin.

39. The method of claim 38 wherein said method comprises exposing the target to an immunoglobulin that has been chemically modified at Fc region lysine groups of the immunoglobulin.

* * * * *